United States Patent [19]

Dillon et al.

[11] Patent Number: 5,735,272
[45] Date of Patent: Apr. 7, 1998

[54] NASAL TUBE HOLDER HAVING A NASAL DILATOR ATTACHED THERETO

[76] Inventors: Michael M. Dillon, 8436 W. Piccadily Rd., Phoenix, Ariz. 85037; David F. Kreitzer, 8220 E. Montecito Ave., Scottsdale, Ariz. 85251; Dan B. Pool, 23 E. Surrey Rd., Phoenix, Ariz. 85029

[21] Appl. No.: 785,130

[22] Filed: Jan. 22, 1997

[51] Int. Cl.⁶ .......................... A61M 15/08; A61M 5/32; A62B 7/00; A61F 5/08
[52] U.S. Cl. ............ 128/207.18; 128/912; 128/DIG. 26; 604/180; 606/204.45
[58] Field of Search ........................ 128/200.24, 207.18, 128/911, 912, DIG. 26; 606/199, 204.45; 604/174, 180

[56] References Cited

U.S. PATENT DOCUMENTS

| | | | |
|---|---|---|---|
| 3,046,989 | 7/1962 | Hill | 128/207.18 |
| 4,340,040 | 7/1982 | Straith | 128/207.18 |
| 4,823,789 | 4/1989 | Beisang, III | 128/207.18 |
| 4,932,943 | 6/1990 | Nowak | 604/180 |
| 5,172,688 | 12/1992 | Dillon | 128/207.18 |
| 5,513,635 | 5/1996 | Bedi | 128/207.18 |
| 5,533,503 | 7/1996 | Doubek et al. | 128/200.24 |
| 5,553,605 | 9/1996 | Muchin | 128/200.28 |

*Primary Examiner*—Kimberly L. Asher
*Attorney, Agent, or Firm*—Robert A. Parsons; Michael W. Goltry; Parsons & Goltry

[57] ABSTRACT

A nasal tube holder for anchoring a tube in a nasal passage including a nasal dilator affixable over the bridge of a nose, a tube holding portion depending from the nasal dilator for engaging a tube and anchoring the tube within a nasal passage and an adhesive backing carried by the nasal dilator and the tube holding portion for adhering the nasal dilator to a nose and a tube to the tube holding portion.

14 Claims, 4 Drawing Sheets

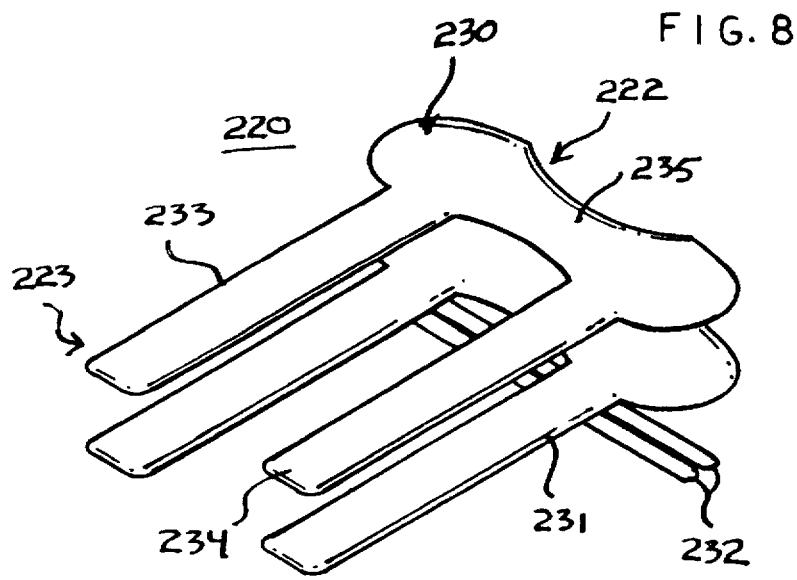
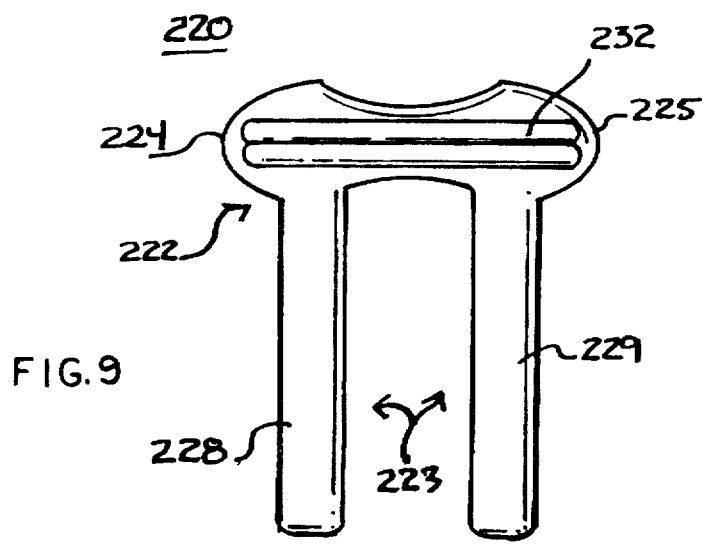

NASAL TUBE HOLDER HAVING A NASAL DILATOR ATTACHED THERETO

BACKGROUND OF THE INVENTION

1. Field of the Invention

This invention relates to medical devices and, more particularly to nasal tube holding and anchoring devices.

2. Prior Art

During the course of certain medical procedures and certain medical conditions, it is necessary to intubate a patient with a nasal-gastric tube, an oxygen tube or other cannula into or through the nasal orifice. A nasal-gastric tube is routed through the patient's nasal passage, the pharynx and esophagus, and into the stomach. After intubation it is very important to prevent movement of the tube. Movement can cause damage to delicate tissues lining the nasal and digestive tract or misalign the tube, rendering it non-functional. To avoid movement of the tube, various anchoring devices have been developed.

In the past, tape cut from a roll was used to secure the tube to a patients face. This can be time consuming as well as less than adequate since the tape can interfere with the patients breathing. Furthermore, taping the tube against a patients face can hold a tube at a less than optimum angle and applies pressure to the tissue surfaces surrounding the nasal opening, leading to irritation and discomfort.

Other devices include adhesive backed pads which adhere to the nose and which support an attachment member such as a hub for receiving a nasal tube or an adhesive strip which engages the nasal-gastric tube. While each of these is superior to tape, they also present some serious drawbacks. Because these devices support the tube with pads anchored to the nose, they can interfere with breathing.

A portion of the human population has some malformation of the nasal passages which makes breathing difficult. Examples of such malformations are a deviated septum and swelling due to allergic reactions or extended use of tubes such as for the delivery of oxygen or nasal gastric tubes. The lower portion of the nostril immediately above the entrance to the nostril is known as a vestibule. The vestibule tapers inwardly to a narrowed neck-like area called the ostium internum. Above the ostium internum the nasal passages widen. Nasal obstructions commonly occur at the ostium in individuals who have swelling due to allergic reactions, a deviated septum irritation from tubes or similar condition. Commonly, the lateral wall at the ostium is loose with the result that the outer wall tissue draws in during the process of inhalation to substantially block the passage of air through the nasal passage.

Blockages of the nasal passages is obviously very frustrating especially if a portion is already blocked by a tube. In particular, sustained mouth breathing over a long period of time may cause lung irritation due to the inhalation of foreign particles that would otherwise be filtered if the breath had been passed through the nose. Blockage of the nasal passages is particularly uncomfortable at night, since it is uncomfortable for many people who have such a problem to breathe through the mouth while asleep. Nasal blockage can lead to sleep disturbances and irregularities because those with such a condition may often wake during the night because of oxygen depletion.

A more serious problem occurs for individuals which need a supply of oxygen, such as those suffering from emphysema or the like. In these cases, lung capacity is reduced, necessitating a higher percentage of inhaled oxygen. The oxygen is typically supplied by tubes or cannula located in the nasal passages. Inhalation through the nose is mandatory to receive the benefit from supplied oxygen. Currently, tubes supplying oxygen are strapped to the nose employing straps encircling the patients head and holding the tube in place. While this is very secure, it can be somewhat uncomfortable.

It would be highly advantageous, therefore, to remedy the foregoing and other deficiencies inherent in the prior art.

Accordingly, it is an object of the present invention to provide a new and improved nasal tube holder.

Another object of the present invention is to provide a nasal tube holder which prevents the outer wall tissue of nasal passages of a nose from drawing in during breathing.

And another object of the present invention is to provide a nasal tube holder that is easy to construct.

Still another object of the present invention is to provide a nasal tube holder that is easy to install.

Yet another object of the instant invention is to provide a nasal tube holder that is comfortable.

Yet still another object of the instant invention is to provide a nasal tube holder that does not disengage during normal wear.

SUMMARY OF THE INVENTION

Briefly, to achieve the desired objects of the instant invention in accordance with a preferred embodiment thereof, provided is a nasal tube holder for anchoring a tube in a nasal passage including a nasal dilator affixable over the bridge of a nose, a tube holding portion depending from the nasal dilator for engaging a tube and anchoring the tube within a nasal passage and an adhesive backing carried by the nasal dilator and the tube holding portion for adhering the nasal dilator to a nose and a tube to the tube holding portion.

In a further embodiment the nasal dilator includes a first end, a second end and an elastic member for traversing the nose and interconnecting the first end and the second end. The elastic member is changeable between an expanded configuration and a contracted configuration for biasing the first end and the second end of the nasal dilator outwardly from the face of the user, whereby the nasal passages are maintained in a dilated condition.

In yet a further embodiment the nasal dilator includes a first end, a second end and a flexible truss for traversing the nose and interconnecting the first end and the second end. The flexible truss is changeable between a flexed configuration and an unflexed configuration for biasing the first end and the second end of the nasal dilator outwardly from the face of the user, whereby the nasal passages are maintained in a dilated condition.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which:

FIG. 8 is an exploded perspective view of a nasal tube holder in accordance with yet another embodiment of the present invention; and FIG. 9 is bottom plan view of the nasal tube holder of FIG. 8.

DETAILED DESCRIPTION OF THE PREFERRED EMBODIMENT

Figure 1:
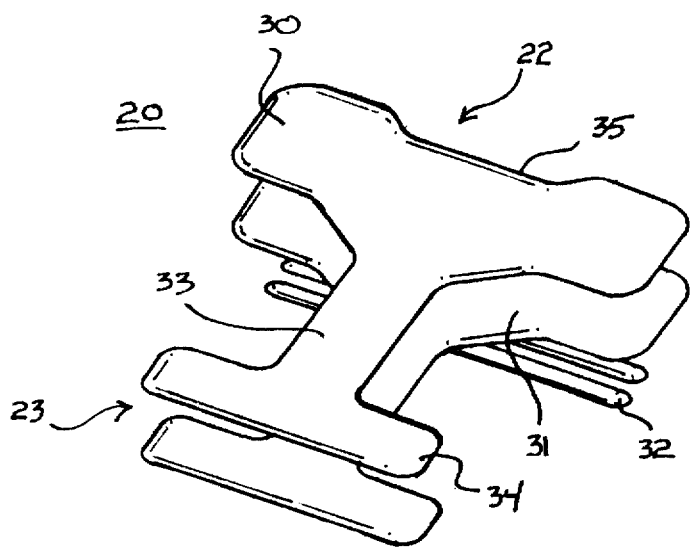
FIG. 1 is an exploded perspective view of a nasal tube holder in accordance with a preferred embodiment of the present invention.
Figure 2:
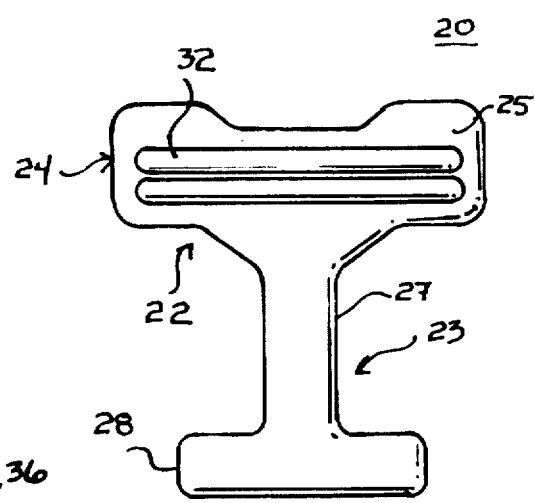
FIG. 2 is bottom plan view of the nasal tube holder of FIG. 1.

Turning now to the drawings, in which like reference characters indicate corresponding elements throughout the several views, attention is first directed to FIGS. 1 and 2 illustrating a nasal tube holder 20. Referring specifically to FIG. 2, nasal tube holder 20 is generally comprised of a nasal dilator 22 and a tube holding portion 23 depending therefrom. Nasal dilator 22 has an elongate shape for bridging the human nose, with opposing ends 24 and 25 which are engagable to opposing sides of the nose. Tube holding portion 23 includes a strip 27 depending generally perpendicularly from nasal dilator 22 and terminating in an elongate pad 28 having a longitudinal axis generally perpendicular to strip 27 and parallel to nasal dilator 22.

With additional reference to FIG. 1, nasal tube holder 20 is composed of three principle layers, a thin flexible body 30, an adhesive backing 31, and biasing members 32. Tube holding portion 23 is preferably integrally formed with nasal dilator 22. In this embodiment this is accomplished by thin flexible body member 30. Body member 30 is formed of a single piece of flexible and breathable material such as gauze, and includes an elongate portion 35 forming a portion of nasal dilator 22, and an elongate strip 33 depending perpendicularly therefrom. Strip 33 terminates in an elongate portion 34 having a longitudinal axis generally perpendicular to strip 33 and parallel to elongate portion 35. Adhesive backing 31 forms a layer which covers the back of body member 30.

Still referring to FIGS. 1 and 2, nasal dilator 22 is completed by biasing members 32 coupled to body member 30 by adhesive backing 31. In this embodiment, biasing members 32 are a pair of resilient truss members changeable between flexed and unflexed configurations. When flexed, the truss members will attempt to return to their unflexed states. The truss members may be formed of substantially any resilient material such as metal, plastic, etc. Biasing members 32 extend longitudinally from proximate end 24 to end 25 of nasal dilator 22.

While not specifically shown, it should be understood that additional adhesive can be applied to the back of biasing members 32 to further insure adhesion to the nose of a patient. Also, protective sheets (not shown) can be applied to adhesive backing 31 for protection prior to use. The protective sheets would be removed to expose adhesive backing 31 prior to application of nasal tube holder 20 to a nose.

Figure 3:
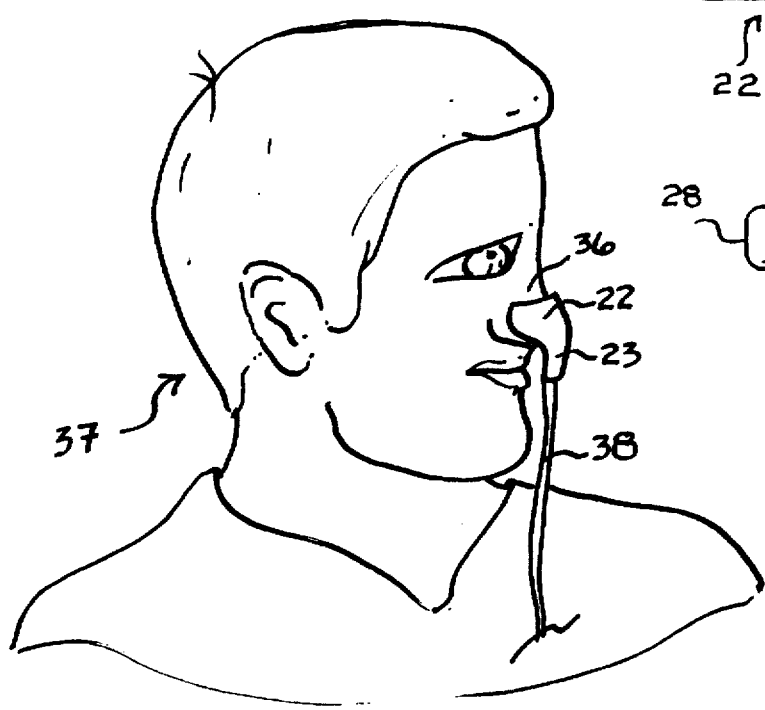
FIG. 3 is a perspective view of the nasal tube holder of FIGS. 1 and 2, as it would appear anchoring a tube to a patient.

Turning now to FIG. 3, nasal tube holder 20 is shown applied to a nose 36 of a patient 37 with ends 24 and 25 adhered to opposing sides of nose 36. Nasal dilator 22 bridges nose 36 with tube holding portion 23 depending therefrom and extending below nose 36. Elongate pad 28 wraps about a nasal gastric tube 38 securely attaching it to nasal tube holder 20 and anchoring it to nose 36. To apply nasal tube holder 20, ends 24 and 25 of nasal dilator are flexed inward to engage opposite sides of nose 36. The outward flexion of biasing members 32 in their attempt to return to their unflexed state holds the nasal passages of the nose open. This allows unobstructed breathing, and aids in keeping contact between tube 38 and the delicate tissues inside nose 36 to a minimum.

Figure 4:
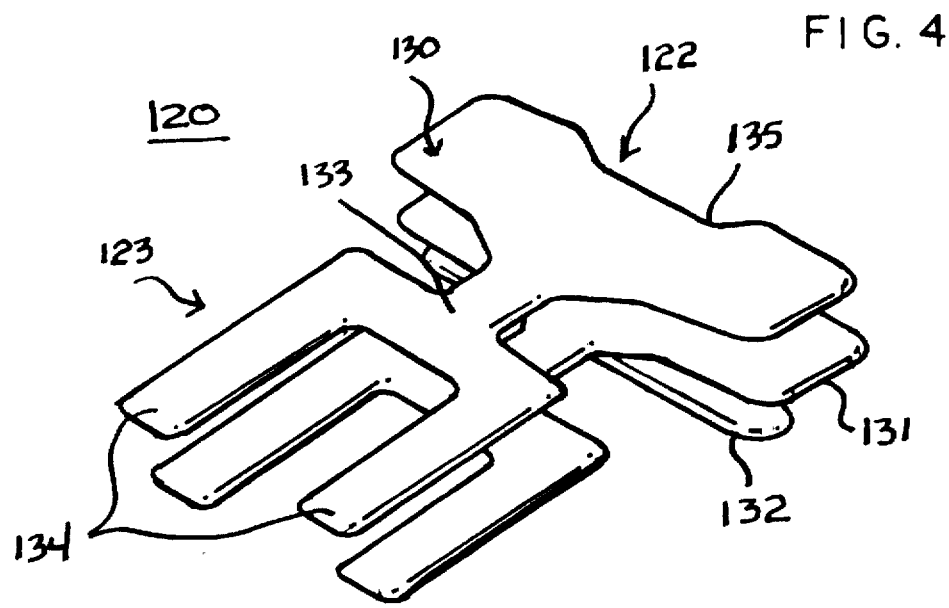
FIG. 4 is an exploded perspective view of a nasal tube holder in accordance with another embodiment of the present invention.
Figure 5:
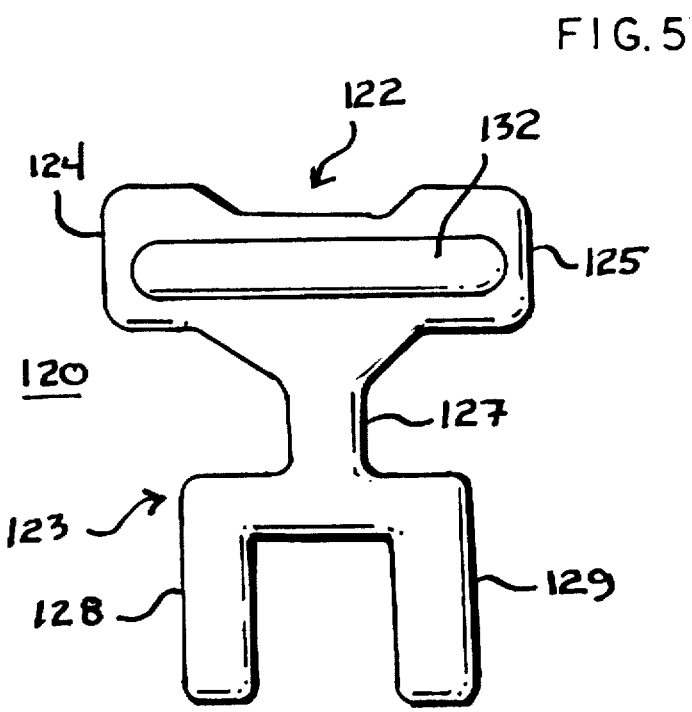
FIG. 5 is bottom plan view of the nasal tube holder of FIG. 4.

Referring now to FIGS. 4 and 5, a further embodiment of a nasal tube holder, generally designated 120 is illustrated. Referring specifically to FIG. 5, nasal tube holder 120 is generally comprised of a nasal dilator 122 and a tube holding portion 123 depending therefrom. Nasal dilator 122 has an elongate shape for bridging the human nose, with opposing ends 124 and 125 which are engagable to opposing sides of the nose. Tube holding portion 123 includes a strip 127 depending generally perpendicularly from nasal dilator 122 and terminating in a pair of parallel spaced apart elongate pads 128 and 129 having a longitudinal axis generally parallel to strip 127 and perpendicular to nasal dilator 122.

With additional reference to FIG. 4, nasal tube holder 120 is composed of three principle layers, a thin flexible body 130, an adhesive backing 131, and a biasing member 132. Tube holding portion 123 is preferably integrally formed with nasal dilator 122. In this embodiment this is accomplished by thin flexible body member 130. Body member 130 is formed of a flexible and breathable material such as gauze, and includes an elongate portion 135 forming a portion of nasal dilator 122, and an elongate strip 133 depending perpendicularly therefrom. Strip 133 terminates in a pair of parallel, spaced apart elongate portions 134 having a longitudinal axis generally parallel to strip 133 and perpendicular to elongate portion 135. Adhesive backing 131 forms a layer which covers the back of body member 130.

Still referring to FIGS. 4 and 5, nasal dilator 122 is completed by biasing member 132 coupled to body member 130 by adhesive backing 131. In this embodiment, biasing members 132 is a single resilient truss member, changeable between flexed and unflexed configurations. When flexed, the truss members will attempt to return to its unflexed state. The truss member may be formed of substantially any resilient material such as metal plastic etc. It should be understood that while single biasing member 132 is shown in this embodiment, two or more can be utilized as illustrated in FIGS. 1 and 2. Furthermore, a single biasing member can be used in the embodiment of FIGS. 1 and 2. Biasing member 132 extends longitudinally from proximate end 124 to end 125 of nasal dilator 122. While not specifically shown, it should be understood that additional adhesive can be applied to the back of biasing member 132 to further insure adhesion to the nose of a patient. Also, protective sheets as described in the previous embodiment can be employed to protect adhesive backing 131. The protective sheets would be removed to expose adhesive backing 131 prior to application of nasal tube holder 120 to a nose.

Figure 6:
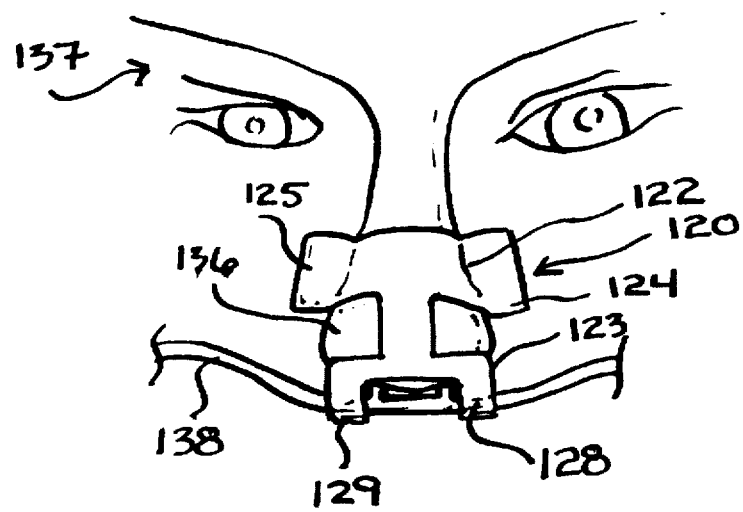
FIG. 6 is a perspective view of the nasal tube holder of FIGS. 4 and 5, as it would appear anchoring an oxygen tube to a patient.
Figure 7:
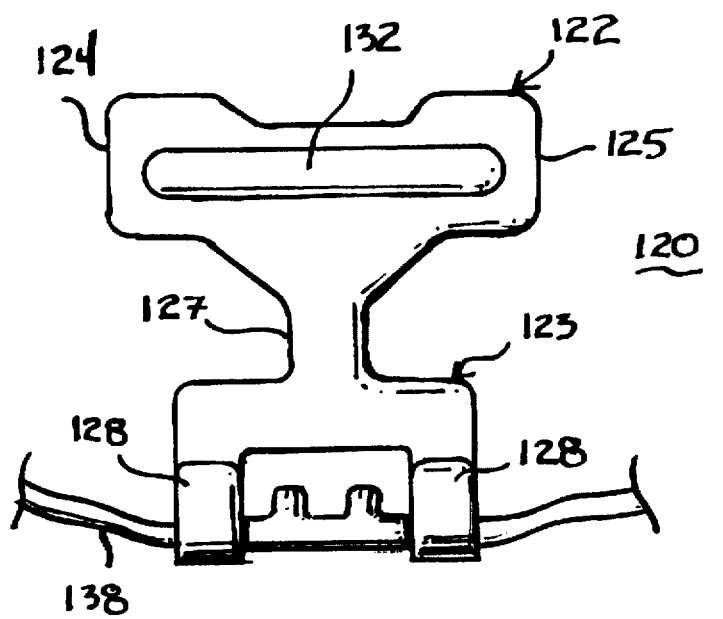
FIG. 7 is an enlarged perspective view of the nasal tube holder of FIGS. 4–6 as it would appear attached to an oxygen tube.

Turning now to FIG. 6, nasal tube holder 120 is shown applied to a nose 136 of a patient 137. Nasal dilator 122 bridges nose 136 with tube holding portion 123 depending therefrom and extending below nose 136. Elongate pads 128 and 129 wrap about an oxygen tube 138 securely attaching it to nasal tube holder 120 and anchoring it to nose 136. With additional reference to FIG. 7, it can be seen that elongate portions 128 and 129 are each folded over and adhered to themselves, with oxygen tube 138 captured in-between. To apply nasal tube holder 120, ends 124 and 125 of nasal dilator 122 are flexed inward to engage opposite sides of nose 136. The outward flexion of biasing member 132 in its attempt to return to its unflexed state holds the nasal passages of the nose open. This allows unobstructed inhalation of the oxygen supplied by oxygen tube 138, and aids in keeping contact between tube 138 and the delicate tissues inside nose 136 to a minimum.

Referring now to FIGS. 8 and 9, yet a further embodiment of a nasal tube holder, generally designated 220 is illustrated. Referring specifically to FIG. 9, nasal tube holder 220 is generally comprised of a nasal dilator 222 and a tube holding portion 223 depending therefrom. Nasal dilator 222 has an elongate shape for bridging the human nose, with opposing ends 224 and 225 which are engagable to opposing sides of the nose. Tube holding portion 223 includes a pair of parallel spaced apart elongate pads 228 and 229 depending generally perpendicularly from nasal dilator 222 proximate ends 224 and 225 respectively. Elongate pads 228 and 229 each have a longitudinal axis generally perpendicular to nasal dilator 222.

With additional reference to FIG. 8, nasal tube holder 220 is composed of three principle layers, a thin flexible body 230, an adhesive backing 231, and a biasing member 232. Tube holding portion 223 is preferably integrally formed with nasal dilator 222. In this embodiment this is accomplished by thin flexible body member 230. Body member 230 is formed of a flexible and breathable material such as gauze, and includes an elongate portion 235 forming a portion of nasal dilator 222, and a pair of parallel, spaced apart elongate portions 233 and 234 depending perpendicularly therefrom. Elongate portions 233 and 234 each have a longitudinal axis generally perpendicular to elongate portion 235. Adhesive backing 231 forms a layer which covers the back of body member 230.

Still referring to FIGS. 8 and 9, nasal dilator 222 is completed by biasing member 232 coupled to body member 230 by adhesive backing 231. In this embodiment, biasing members 232 is an elastic member, changeable between expanded and contracted configurations. When expanded or stretched, the truss members will attempt to return to its contracted or unstretched state. In this embodiment, body member 230 is formed of a material which can be expanded and contracted. Gauze has this characteristic, allowing body member 230 to expand and contract with the elastic member.

It should be understood that while single biasing member 232 is shown in this embodiment, two or more can be utilized as illustrated in FIGS. 1 and 2. Furthermore, the biasing members of each of the embodiments may be interchanged with any of the others. Biasing member 232 extends longitudinally from proximate end 224 to end 225 of nasal dilator 222. While not specifically shown, it should be understood that additional adhesive can be applied to the back of biasing member 232 to further insure adhesion to the nose of a patient. Also, protective sheets as described in the previous embodiments can be employed to protect adhesive backing 231. The protective sheets would be removed to expose adhesive backing 231 prior to application of nasal tube holder 220 to a nose.

To apply nasal tube holder 220, the distance between ends 224 and 225 of nasal dilator 222 is increased by pulling them apart. The dilator is then applied to opposing sides of the nose as shown with embodiment 120 in FIG. 6. The bias produced by biasing member 232 as it attempts to contract back to its original length, opens the nasal passages of the nose. Tube holding portion 223 operates in substantially the same manner as tube holding portion 123 shown in FIGS. 6 and 7, and will not be repeated.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A nasal tube holder for anchoring a tube in a nasal passage, comprising:

a nasal dilator affixable over the bridge of a nose, the nasal dilator including a first end, a second end and biasing means for biasing said first end and said second end of the nasal dilator outwardly from the face of the user whereby the nasal passages are maintained in a dilated condition;

a tube holding portion depending from the nasal dilator, for engaging a tube and anchoring the tube within a nasal passage; and an adhesive backing carried by the nasal dilator and the tube holding portion for adhering the nasal dilator to a nose and a tube to the tube holding portion.

2. A nasal tube holder as claimed in claim 1, wherein the biasing means includes a flexural elastic element traversing the nose, interconnecting the first end and the second end and changeable between an expanded configuration and a contracted configuration.

3. A nasal tube holder as claimed in claim 1, wherein the biasing means is a flexible truss changeable between a flexed configuration and an unflexed configuration.

4. A nasal tube holder as claimed in claim 1, wherein the tube holding portion comprises a strip depending from the nasal dilator and terminating in an elongate pad having a longitudinal axis perpendicular to the strip.

5. A nasal tube holder as claimed in claim 4, wherein the tube holding portion further includes a pair of a pair of parallel, spaced apart elongate pads having a longitudinal axis generally parallel to the strip and perpendicular to the elongate portion.

6. A nasal tube holder as claimed in claim 1, wherein the tube holding portion includes a pair of parallel spaced apart elongate pads depending generally perpendicularly from the nasal dilator proximate the first and second ends respectively, the elongate pads each have a longitudinal axis generally perpendicular to the nasal dilator.

7. A nasal tube holder for anchoring a tube in a nasal passage, comprising:

a nasal dilator affixable over the bridge of a nose, the nasal dilator including a first end, a second, end and a elastic member for traversing the nose and interconnecting the first end and the second end, the elastic biasing member means changeable between an expanded configuration and a contracted configuration for biasing said first end and said second end of the nasal dilator outwardly from the face of the user whereby the nasal passages are maintained in a dilated condition;

a tube holding portion depending from the nasal dilator, for engaging a tube and anchoring the tube within a nasal passage; and an adhesive backing carried by the nasal dilator and the tube holding portion for adhering the nasal dilator to a nose and a tube to the tube holding portion.

8. A nasal tube holder as claimed in claim 7, wherein the tube holding portion comprises a strip depending from the nasal dilator and terminating in an elongate pad having a longitudinal axis perpendicular to the strip.

9. A nasal tube holder as claimed in claim 8, wherein the tube holding portion further includes a pair of a pair of parallel, spaced apart elongate pads having a longitudinal axis generally parallel to the strip and perpendicular to the elongate portion.

10. A nasal tube holder as claimed in claim 7, wherein the tube holding portion includes a pair of parallel spaced apart elongate pads depending generally perpendicularly from the nasal dilator proximate the first and second ends respectively, the elongate pads each have a longitudinal axis generally perpendicular to the nasal dilator.

11. A nasal tube holder for anchoring a tube in a nasal passage, comprising:

a nasal dilator affixable over the bridge of a nose, the nasal dilator including a first end, a second end and a flexible truss biasing means for traversing the nose and interconnecting the first end and the second end, the flexible truss biasing means changeable between a flexed configuration and an unflexed configuration for biasing the first end and the second end of the nasal dilator outwardly from the face of the user whereby the nasal passages are maintained in a dilated condition;

a tube holding portion depending from the nasal dilator, for engaging a tube and anchoring the tube within a nasal passage; and an adhesive backing carried by the nasal dilator and the tube holding portion for adhering the nasal dilator to a nose and a tube to the tube holding portion.

12. A nasal tube holder as claimed in claim 11, wherein the tube holding portion comprises a strip depending from the nasal dilator and terminating in an elongate pad having a longitudinal axis perpendicular to the strip.

13. A nasal tube holder as claimed in claim 12, wherein the tube holding portion further includes a pair of a pair of parallel, spaced apart elongate pads having a longitudinal axis generally parallel to the strip and perpendicular to the elongate portion.

14. A nasal tube holder as claimed in claim 11, wherein the tube holding portion includes a pair of parallel spaced apart elongate pads depending generally perpendicularly from the nasal dilator proximate the first and second ends respectively, the elongate pads each have a longitudinal axis generally perpendicular to the nasal dilator.

* * * * *